US006881409B2

(12) United States Patent
Gold

(10) Patent No.: US 6,881,409 B2
(45) Date of Patent: *Apr. 19, 2005

(54) COMPOSITIONS AND METHODS FOR PROMOTING NERVE REGENERATION

(75) Inventor: Bruce G. Gold, West Linn, OR (US)

(73) Assignee: Oregon Health and Science University, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/656,701

(22) Filed: Sep. 4, 2003

(65) Prior Publication Data

US 2004/0063610 A1 Apr. 1, 2004

Related U.S. Application Data

(63) Continuation of application No. 09/825,243, filed on Apr. 2, 2001, now Pat. No. 6,641,810, which is a continuation of application No. 09/326,728, filed on Jun. 7, 1999, now abandoned, which is a continuation of application No. 08/956,691, filed on Oct. 24, 1997, now Pat. No. 5,968,921.

(51) Int. Cl.[7] ................... A61K 39/395; A61K 31/445; A01N 43/30
(52) U.S. Cl. ................... 424/145.1; 514/183; 514/330; 514/423; 514/428; 514/465; 514/466
(58) Field of Search .......................... 424/145.1, 130.1; 514/183, 330, 423, 428, 465, 466, 1, 2

(56) References Cited

U.S. PATENT DOCUMENTS

| 5,026,381 A | 6/1991 | Li |
| 5,192,773 A | 3/1993 | Armistead et al. |
| 5,330,993 A | 7/1994 | Armistead et al. |
| 5,516,797 A | 5/1996 | Armistead et al. |
| 5,525,523 A | 6/1996 | Soldin |
| 5,543,423 A | 8/1996 | Zelle et al. |
| 5,612,350 A | 3/1997 | Or et al. |
| 5,614,547 A | 3/1997 | Hamilton et al. |
| 5,620,971 A | 4/1997 | Armistead et al. |
| 5,622,970 A | 4/1997 | Armistead et al. |
| 5,639,592 A | 6/1997 | Evans et al. |
| 5,780,484 A | 7/1998 | Zelle et al. |
| 5,811,434 A | 9/1998 | Zelle et al. |
| 5,840,736 A | 11/1998 | Zelle et al. |
| 5,968,921 A | 10/1999 | Gold |
| 6,037,370 A | 3/2000 | Armistead |

FOREIGN PATENT DOCUMENTS

| WO | WO 92/04370 | 3/1992 |
| WO | WO 92/19593 | 11/1992 |
| WO | WO 92/19745 | 11/1992 |
| WO | WO 92/21313 | 12/1992 |
| WO | WO 93/07269 | 4/1993 |
| WO | WO 93/23548 | 11/1993 |
| WO | WO 96/40140 | 12/1996 |
| WO | WO 96/40633 | 12/1996 |
| WO | WO 97/18828 | 5/1997 |
| WO | WO 98/20891 | 5/1998 |
| WO | WO 98/20892 | 5/1998 |
| WO | WO 98/20893 | 5/1998 |
| WO | WO 99/21552 | 5/1999 |

OTHER PUBLICATIONS

US 5,654,332, 8/1997, Armistead (withdrawn)
Abstract, J. Biol. Chem., 252(1):308–317, 1977.

(Continued)

Primary Examiner—Elizabeth Kemmerer
Assistant Examiner—Christopher James Nichols
(74) Attorney, Agent, or Firm—Klarquist Sparkman, LLP

(57) ABSTRACT

FK506 and geldanamycin promote nerve regeneration by a common mechanism that involves the binding of these compounds to polypeptide components of steroid receptor-complexes other than the steroid hormone binding portion of the complex (FKBP52 and hsp90, respectively). These and other agents cause hsp90 dissociation from steroid receptor complexes or block association of hsp90 with steroid receptor complexes.

30 Claims, 7 Drawing Sheets

FK506

V-10,367

OTHER PUBLICATIONS

Abstract, *Biochem.*, 31(9):2482–91, 1992.
Abstract, *Mol. Endocrinol.*, 7(11):1418–29, 1993.
Abstract, *J. Clin. Investigation*, 99(6):1217–23, 1997.
Armistead et al., Design, Synthesis and Structure of Non–macrocyclic Inhibitors of FKBP12, the Major Binding Protein for the Immunosuppressant FK506, *Acta Cryst* D51:522–528 (1995).
Bozzo et al., *Exp. Cell Res.*, 214:313–22, 1994.
Buttemeyer et al., *Transpl. Proc.*, 27:1877–1878, 1995.
Buttemeyer et al., *Ann. Plast. Surg.*, 35:396–401, 1995.
Czar et al., Geldanamycin, a Heat Shock Protein 90–Binding Benzoquinone Ansamycin, Inhibits Steroid–Dependent Translocation of the Glucocorticoid Receptor from the Cytoplasm to the Nucleus, *Biochemistry* 36:7776–7785 (1997).
David et al., *Science*, 214:931–33, 1991.
Jackowski et al., *Brit. J. Neurosurg.*, 9:303–317, 1995.
Lee et al., Peripheral Nerve Injury and Repair, *J. Am. Acad. Orthop. Surg.*, 8(4):243–252, 2000.
Miller et al., *J. of Neurochemistry*, 60:2134–44, 1993.
Owens–Grillo et al., The Cyclosporin A–binding Immunophilin CyP–40 and the FK506–binding Immunophilin hsp56 Bind to a Common Site on hsp90 and Exist in Independent Cytosolic Heterocomplexes with the Untransformed Glucocorticoid Receptor, *The Journal of Biological Chemistry* 270:20479–20484 (1995).
Owens–Grillo et al., Binding of Immunophilins to the 90 kDa Heat Shock Protein (hsp90) via a Tetratricopeptide Repeat Domain Is a Conserved Protein Interaction in Plants, *Biochemistry* 35:15249–15255 (1996).
Pratt, W.B., The Role of the hsp90–based Chaperone System in Signal Transduction by Nuclear Receptors and Receptors Signaling Via MAP Kinase, *Annu. Rev. Pharmacol. Toxicol.* 37:297–326 (1997).
Pratt, W.B. and Toft, D.O., Steroid Receptor Interactions with Heat Shock Protein and Immunophilin Chaperones, *Endocrine Reviews* 18:306–360 (1997).
Preis et al., *Cancer Res.*, 48:6530–34, 1988.

Ratajczak, T. and Carrello, A. Cyclophilin 40 (CyP–40), Mapping of Its hsp90 Binding Domain and Evidence That FKBP52 Competes with CyP–40 for hsp90 Binding, *The Journal of Biological Chemistry*, 271:2961–2965 (1996).
Sanchez, E.R. and Ning, Y–M., Immunophilins, Heat Shock Proteins, and Glucocorticoid Receptor Actions in Vivo, *Methods* 9:188–200 (1996).
Schawab, Repairing the Injured Spinal Cord, *Science*, 295:1029–1031, Feb. 8, 2002.
Segnitz and Gehring, The Function of Steroid Hormone Receptors is Inhibited by the hsp90–specific Compound Geldanamycin, *The Journal of Biological Chemistry* 272:18694–18701 (1997).
Smith et al., Progesterone Receptor Structure and Function Altered by Geldanamycin, an hsp90–Binding Agent, *Molecular and Cellular Biology* 15:6804–6812 (1995).
Smith, *Elements of Molec. Neurobio.*, $2^{nd}$ ed., p. 141–142, (1996).
Stancato et al., The hsp90–binding Antibiotic Geldanamycin Decreases Raf Levels and Epidermal Growth Factor Signaling without Disrupting Formation of Signaling Complexes or Reducing the Specific Enzymatic Activity of Raf Kinase, *The Journal of Biological Chemistry* 272:4013–4020 (1997).
Stebbins et al., Crystal Structure of an Hsp90–Geldanamycin Complex: Targeting of a Protein Chaperone by an Antitumor Agent, *Cell* 89:239–250 (1997).
Tanzer L. and Jones K.J., Gonadal Steroid Regulation of Hamster Facial Nerve Regulation: Effects of Dihydrotestosterone and Estradiol, *Experimental Neurology* 146:258–264 (1997).
Wells et al., *Exp. Neurol.*, 146:395–402, 1997.
Whitesell et al., *Cancer Res.*, 52:1721–28, 1992.
Whitesell et al., Inhibition of Heat Shock Protein HSP90–$pp60^{v-src}$ Heteroprotein Complex Formation by Benzoquinone Ansamycins: Essential Role for Stress Proteins in Oncogenic Transformation, *Proc. Natl. Acad. Sci. USA* 91:8324–8328 (1994).

FK506

V-10,367

COMPOSITIONS AND METHODS FOR PROMOTING NERVE REGENERATION

PRIORITY CLAIM

This application is a continuation of U.S. patent application Ser. No. 09/825,243, filed Apr. 2, 2001, now U.S. Pat. No. 6,641,810, which is a continuation of U.S. patent application Ser. No. 09/326,728, filed Jun. 7, 1999, now abandoned, which is a continuation of U.S. patent application Ser. No. 08/956,691, filed Oct. 24, 1997, now issued as U.S. Pat. No. 5,968,921.

BACKGROUND OF THE INVENTION

Following traumatic or mechanically induced axonal degeneration in the peripheral nervous system, axonal regeneration ensues, resulting in functional recovery. However, the rate of axonal elongation (3–4 mm/day) is slow. Consequently, recovery is measured in weeks or months, depending upon the distance between the site of injury and the target tissue. Therapies that speed regeneration over long distances would be highly beneficial to patients and would significantly reduce health care costs.

The immunosuppressant drug FK506 (USAN tacrolimus; Prograf®) speeds functional recovery and axonal regeneration in the rat in a dose-dependent manner following a sciatic nerve crush lesion (Gold et al., *J. Neurosci.* 15:7505–7516, 1995; Gold et al., *Restor. Neurol. Neurosci.* 6:287–296, 1994). FK506 was shown to stimulate neuritic outgrowth in a rat pheochromocytoma cell line in a concentration-dependent manner (Lyons et al., *Proc. Natl. Acad. Sci. USA* 91:3191–3195, 1994).

Systemic administration of two synthetic FK506 analogs that bind FKBP-12 but that do not inhibit calcineurin activity (and which are not immunosuppressants) increases the size of myelinated fibers (Steiner et al., *Nature Medicine* 3:1–8, 1997; Steiner et al., *Proc. Natl. Acad. Sci. USA* 94:2019–2024, 1997). U.S. Pat. No. 5,654,332 (Armistead et al.) discusses immunosuppressive FK506 analogs that bind FKBP12 and that are said to stimulate neurite outgrowth in the presence of NGF. It was stated that the neurotrophic activity of these FKBP12 binding compounds "is directly related to their affinity for FKBP12 and their ability to inhibit FKBP12 rotomase activity" (id. at col. 7, lines 47–50).

It has been reported that androgens and estrogens stimulate facial nerve regeneration in hamsters (Jones, "Androgenic enhancement of motor neuron regeneration," In: Luine and Harding, eds., *Hormonal Restructuring of the Adult Brain,* Ann. N.Y. Acad. Sci. 85:141–164, 1994; Tanzer and Jones, *Exp. Neurol.* 146:258–264, 1997).

SUMMARY OF THE INVENTION

I have discovered that geldanamycin and FK506 stimulate nerve regeneration via a common mechanism. Both compounds bind to polypeptide components of steroid receptor complexes, hsp90 and FKBP52, respectively. These and other compounds that cause hsp90 dissociation from steroid receptor complexes or that block association of hsp90 with steroid receptor complexes stimulate nerve cell growth and promote nerve regeneration. Such compounds can act directly by binding to hsp90 (as in the case of geldanamycin) or indirectly by binding to another polypeptide in the steroid receptor complex (as in the case of FK506 binding of FKBP52).

According to one aspect of the invention, pharmaceutical compositions are provided that include a nerve growth stimulating amount of a non-FKBP12-binding agent that binds to a polypeptide component of a steroid receptor complex other than the ligand (i.e., steroid hormone) binding portion thereof (such polypeptide components including, but not limited to, hsp90 or FKBP52) and a pharmaceutically acceptable excipient. Without limitation to any particular mechanism of action, binding of such agents to the polypeptide component likely causes hsp90 dissociation from the complex or prevents hsp90 association with the complex. Nerve growth promoting agents according to the invention include, but are not limited to non-FKBP2-binding FK506 analogs, benzoquinone ansamycins (e.g., geldanamycin and derivatives thereof), peptides that comprise a sequence of a selected polypeptide component of the complex at a site of interaction between the selected component and another component of the complex, antibodies that bind a polypeptide component of the steroid receptor complex, and combinations thereof.

According to another aspect of the invention, such pharmaceutical compositions include other active ingredients, including, but not limited to, neurotrophic factor other than the nerve growth promoting agent (e.g., NGF, IGF-1, aFGF, bFGF, PDGF, BDNF, CNTF, GDNF, NT-3, NT 4/5, or mixtures thereof), and a steroid ligand of the steroid receptor complex (e.g., estrogen and dexamethasone, as in the Examples below).

According to another aspect of the invention, a transection (severing of the nerve) of a periphal nerve or a spinal cord injury of a mammal is treated by methods that include administering a nerve growth stimulating amount of a non-FKBP12-binding nerve growth promoting agent to the mammal and grafting to the peripheral nerve or spinal cord an allograft or an artificial nerve graft. In the case of a transected peripheral nerve or spinal cord, the space between the transected ends of the peripheral nerve or spinal cord is preferably filled with a material such as collagen, methyl cellulose, etc., or a cell suspension that promotes nerve cell growth, such as Schwann cells and olfactory and sheathing cells. The nerve growth promoting agent can be included together with with such filling materials.

According to another aspect of the invention, pharmaceutical compositions are provided that include a nerve growth stimulating amount of a non-FKBP12-binding FK506 analog that binds to FKBP52 and a pharmaceutically suitable excipient.

According to another aspect of the invention, pharmaceutical compositions are provided that include a nerve growth stimulating amount of an agent that binds to hsp90 and causes hsp90 dissociation from a steroid receptor complex or prevents hsp90 association with the complex and a pharmaceutically suitable excipient.

According to another aspect of the invention, methods of stimulating nerve cell growth in a mammal are provided that include administering a pharmaceutical composition as described herein.

According to another aspect of the invention, methods are provided for stimulating growth of a nerve cell that include contacting the nerve cell with a non-FKBP12-binding agent that binds to a polypeptide component of a steroid receptor complex other than the steroid hormone binding portion thereof and causes hsp90 dissociation from the complex or blocks association of hsp90 with the complex.

According to another aspect of the invention, methods of identifying compounds that stimulate nerve cell growth are provided that include the steps of assaying test compounds for binding to a component of a steroid receptor complex other than the steroid hormone binding portion thereof, and assaying the binding compounds for stimulation of nerve cell growth. In addition, the binding compounds can be assayed for activity in dissociation of hsp90 from the complex or blocking association of hsp90 with the complex.

The foregoing and various features and advantages of the invention will become more apparent from the following detailed description and accompanying drawings.

BRIEF DESCRIPTION OF THE DRAWINGS

FIG. 2: control cells (untreated). FIG. 3: NGF only (10 ng/mL). FIG. 4: geldanamycin (1 nM)+NGF (10 ng/mL). FIG. 5: geldanamycin (10 nM)+NGF (10 ng/mL). FIG. 6: FK506 (10 nM)+NGF (10 ng/mL). FIG. 7: geldanamycin (1 nM)+FK506 (10 nM)+NGF (10 ng/mL). FIG. 8: geldanamycin (10 nM)+FK506 (10 nM)+NGF (10 ng/mL).

FIG. 9: control cells (untreated). FIG. 10: NGF only (10 ng/mL). FIG. 11: FK506 (1 nM)+NGF (10 ng/mL). FIG. 12: FK506 (10 nM)+NGF (10 ng/mL) FIG. 13: geldanamycin (0.1 nM)+NGF (10 ng/mL). FIG. 14: geldanamycin (0.1 nM)+FK506 (1 nM)+NGF (10 ng/mL). FIG. 15: geldanamycin (0.1 nM)+FK506 (10 nM)+NGF (10 ng/mL).

DETAILED DESCRIPTION

Figure 1:
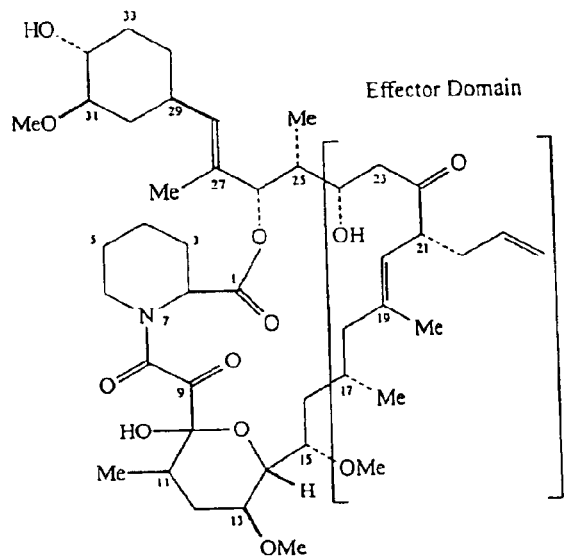
FIG. 1 shows structures of FK506 (left) and a representative FK506 analog, V-10, 367 (right). The bracketed portion of FK506 represents the calcineurin-binding domain, which is absent in V-10, 367.
Figure 1:
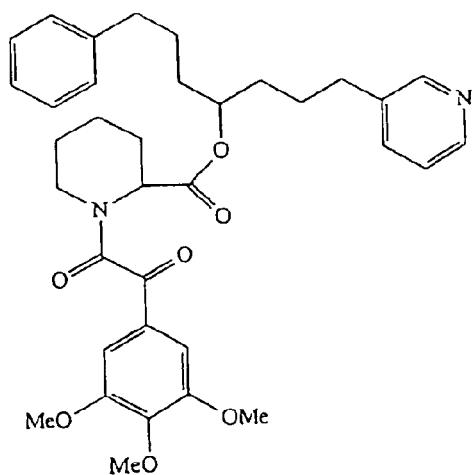

Members of the steroid/thyroid receptor family, including steroid receptors such as the glucocorticoid and progesterone receptors, act as ligand-inducible enhancers of specific gene expression.

Upon translation, steroid receptors are assembled into multiprotein complexes. Steroid receptors exist in two states that are in dynamic equilibrium in the cell. An initial hormone receptor complex includes the steroid receptor, hsp90, hsp70, and at least two co-chaperones, p60 and Hip (p48). This initial complex is localized in the cytosol and does not bind DNA or enhance specific gene transcription. The initial complex is in equilibrium with a metastable, nearly mature complex that lacks hsp90, p60, and Hip but includes p23 and one of the three large immunophilins, FKBP52 (also called hsp56), FKBP54, or CyP40, and under some circumstances, hsp 70 (Smith et al., Mol. Cell. Biol. 15:6804–6812, 1995; Dittmar et al., J. Biol. Chem. 271:12833–12839, 1996). The nearly mature complex is competent to bind hormone; upon hormone binding, the receptor is released as an active transcription factor (Smith et al., Mol. Cell. Biol. 15:6804–6812, 1995; Dittmar et al., J. Biol. Chem. 271:12833–12839, 1996). Steroid receptor complexes are constantly dissociating and reforming under physiological conditions.

Hsp90-mediated conformational maturation is required for nuclear hormone receptors to acquire or maintain a state competent to bind hormone (Smith et al., Mol. Cell. Biol. 15:6804–6812, 1995; Dittmar et al., J. Biol. Chem. 271:12833–12839, 1996). Geldanamycin, a benzoquinone ansamycin antibiotic, binds in a pharmacologically specific manner to hsp90 (Whitesell et al., Proc. Natl. Acad. Sci. USA 91:8324–8328, 1994) and prevents association of the p23 component of the heterocomplex assembly system with hsp90 (Johnson and Toft, Mol. Endocrinol. 9:670–678, 1995). Geldanamycin permits dissociation of a steroid receptor complex, permitting receptors to be transformed (i.e., dissociated from hsp90), but blocks reassembly of the hormone-responsive form of the complex, thereby preventing hormone activation and ultimately resulting in the degradation of the hormone receptor. Geldanamycin blocks assembly of the progesterone receptor (PR) complex (Smith. et al., Mol. Cell. Biol. 15:6804–6812, 1995) and of the glucocorticoid receptor (GR) complex (Czar et al., Biochem. 36:7776–7785, 1997) at an intermediate stage of assembly where the hormone binding domain is not properly folded and therefore cannot bind steroid. Geldanamycin also is known to act on estrogen and androgen hormone receptors (Smith et al., Mol. Cell. Biol. 15:6804–6812, 1995; Nair et al., Cell Stress and Chaperones 1:237–250, 1996). Transformation of GR and PR as measured either by 9S to 4S conversion or by acquisition of DNA-binding activity is correlated with dissociation of steroid receptors from hsp90 (see, e.g., Meshinchi et al., J. Biol. Chem. 265:4863–4870, 1990; Kost et al., Mol. Cell. Biol. 9:3829–3838, 1989).

In addition to steroid receptors, other "substrate proteins" for hsp90 include v-erbA, dioxin receptor, sim, myoD1, E12, heat shock factor, tumor promoter-specific binding protein, hepatitis B reverse transcriptase, p53 tumor suppressor mutant, various protein kinases (e.g., the tyrosine kinases v-src, c-src, v-fps, v-yes, v-fes, v-frg, c-frg, lck, Wee1 kinase, and sevenless PTK), heme-regulated eIF-2α, eEF-2 kinase, casein kinase II, v-raf, c-raf, Gag-Mil, MEK, PI-4 kinase, actin, tubulin, centrin, proteasome, and $G_{\beta\gamma}$ complex (reviewed in Pratt and Toft, Endocrine Rev. 18:306–360, 1997).

FKBP52 is a member of the FK506-binding class of immunophilins. Binding of FK506 to GR-associated FKBP52 caused increased nuclear translocation of GR in response to dexamethasone and potentiation of GR-mediated gene expression (Sanchez and Ning, METH-ODS: A Companion to Meth. Enzymol. 9:188–200, 1996). Dexamethasone-induced GR-specific gene expression is also potentiated by cyclosporin A (CsA) (Renoir et al., Proc. Natl. Acad. Sci. USA 92:4977–4981, 1995), rapamycin (Ning and Sanchez, J. Biol. Chem. 268:6073–6076, 1993), and nonimmunosuppressive analogs of FK506 (e.g., 15-o-desmethyl FKS20) or of CsA (e.g., CsH and SDZ220384) (Sanchez and Ning, METHODS: A Companion to Meth. Enzymol. 9:188–200, 1996).

CyP40, rather than FKBPS2, is the target for binding of CsA and its analogs (Sanchez and Ning, METHODS: A Companion to Meth. Enzymol. 9:188–200, 1996). FKBP52 and CyP40 bind directly to hsp90, and CyP40 competes for FKBP52 binding to hsp90 and vice versa. The immunophilins bind hsp90 in a mutually exclusive fashion, leading to the formation of separate CyP40-hsp90 and FKBP52-hsp90 complexes (Ratajczak and Carrello, J. Biol. Chem. 271:2961–2965, 1996). Immunophilins such as FKBP52 and CyP40 and non-immunophilin proteins such as PP5, p60, and Mas70p, have one or more tetratricopeptide repeat (TPR) domains (Ratajczak et al., J. Biol. Chem. 268:13187–13192, 1993) that bind to the TPR-binding domain of hsp90. The number of TPR domains in a protein appears to correlate with its hsp90-binding affinity. Regions bordering the TPR domain also participate in binding, e.g., the acidic domain at the N-terminal end of bovine CyP40 (residues 185–225) and FKBP52 (residues 232–271) and the calmodulin binding region at the C-terminus of bovine CyP40 (Ratajczak and Carrello, *J. Biol. Chem.* 271:2961–2965, 1996). Binding of both FKBP52 and CyP40 to hsp90 is competed by a purified fragment of human CyP40 comprising its three TPR domains and by a fragment of rat PPS comprising its four TPR domains (reviewed in Pratt and Toft, *Endocrine Rev.* 18:306–360, 1997).

In addition to multiple TPR binding domains, FKBP52 contains a sequence (EDLTDDED in rabbit; SEQ ID NO: 1) that is retained with conservative replacements in human and mouse. This negatively charged sequence is electrostatically complementary to the receptor nuclear localization signals (e.g., the NL1 sequence RKTKKKIK of rat GR; SEQ ID NO: 2). An antibody raised against the conserved negatively charged sequence impeded the dexamethasone-mediated shift of the GR into the nucleus (reviewed in Pratt and Toft, *Endocrine Rev.* 18:306–360, 1997). It has also been reported that antibodies directed against a conserved negatively-charged sequence of FKBP52 impede dexamethasone-mediated cytophasmic-nuclear translocation of GR (Czar et al., *Mol. Endocrinol.* 9:1549–1560, 1995).

The effects of FK506 and geldanamycin on nerve regeneration likely result from the binding of these compounds to components of steroid receptor complexes, causing the dissociation of hsp90 from the steroid receptor complex either directly (by binding to hsp90 or interfering with the binding of hsp90 to the steroid receptor) or indirectly (by binding to a polypeptide such as FKBP52 that itself binds to hsp90), or, alternatively, by preventing association of hsp90 with the steroid receptor complex. However, interference with the ability of hsp90 to complex with and perform its chaperone function for other hsp90 substrate proteins may also be responsible for or contribute to the observed stimulation of nerve regeneration by FK506 and/or geldanamycin.

Definitions and Methods

"Nerve growth promoting agent" (NGPA). A "nerve growth promoting agent" or NGPA is defined as a substance that binds to a polypeptide component of a steroid receptor complex other than the steroid hormone binding portion thereof, such components including but not limited to hsp90 and FKBP52, and promotes nerve regeneration, without limitation to a particular mechanism of action. Preferably, the NGPA does not bind FKBP12 and is non-immunosuppressive. NGPAs include, but are not limited to, non-FKBP12-binding ("non-binding") analogs of FK506; benzoquinone ansamycins, including geldanamycin, naturally occurring analogs of geldanamycin, including, but not limited to, herbimycin A and macbecin (DeBoer et al., *J. Antibiot.* (Tokyo) 23:442–447, 1970; Omura et al., *J. Antibiot.* (Tokyo) 32:255–261, 1979; Ono et al., *Gann.* 73:938–944, 1992), and derivatives thereof; peptides including an amino acid sequence of a particular polypeptide component of a steroid receptor complex at a site of interaction between that component and another component of the complex (such as the TPR domain), and antibodies that bind specifically to polypeptide components of steroid receptor complexes, e.g., anti-hsp90, anti-FKBP52, etc.) and interfere with the interaction of the bound polypeptide with another polypeptide in the steroid receptor complex.

"Steroid receptor complex" or "steroid hormone receptor" and "component" thereof; "transformation"; "activation". The term "steroid receptor complex" is intended to encompass a multiprotein complex associated with any steroid receptor, including, but not limited to, the progesterone receptor, glucocorticoid receptor, estrogen receptor, androgen receptor, and mineralocorticoid receptor. A polypeptide "component" is a polypeptide other than the steroid hormone binding portion of the steroid receptor complex, and preferably other than steroid receptor (particularly the steroid hormone binding portion thereof), such as hsp90, FKBP52, etc., that is part of a steroid receptor complex.

The term "transformation" refers to the conversion of the 9S non-DNA-binding form of a steroid receptor complex to the 4S DNA-binding form. The term "activation" refers to the conversion of a steroid receptor from a form that does not bind steroid to a steroid-binding form.

Assays for Identifying NGPAs. There are a number of well-known methods for assaying compounds that bind to hsp90, FKBP52, and other polypeptide components of a steroid receptor complex that can be used as an initial screen for candidate compounds that stimulate nerve regeneration. Compounds can subsequently be tested in vitro or in vivo for activity in stimulating nerve regeneration.

For example, one may assay for the binding of a test compound to a polypeptide that is a component of a steroid receptor complex. An assay for binding to hsp90 is described, for example, by Whitesell et al. (*Proc. Natl. Acad. Sci. USA* 91:8324–8328, 1994). Commercial hsp90 (StressGen Biotechnologies, Victoria, BC) dissolved in 20 $\mu$g/mL of TNESV buffer (50 mM Tris-HCl, pH 7.4/1% Nonidet P-40/2 mM EDTA/100 mM NaCl/1 mM orthovanadate/1 mM phenylmethylsulfonyl fluoride/20 $\mu$g leupeptin per mL/20 $\mu$g of aprotinin per ml) and the test compound are incubated for 45 min at 4° C. with geldanamycin immobilized on a conventional solid support, e.g., geldanamycin-coupled agarose beads (Whitesell et al., *Proc. Natl. Acad. Sci. USA* 91:8324–8328, 1994. The beads are then washed with TNESV buffer and bound hsp90 is eluted by heating in reducing loading buffer and can be analyzed by SDS/PAGE and silver staining (Bio-Rad), for example. Alternatively, if the hsp90 is labeled, one can assay for bound label versus free label. Test compounds that compete with geldanamycin for binding to hsp90 inhibit the binding of solubilized hsp90 to the beads.

Similar assays can be performed to identify compounds that bind other steroid receptor complex polypeptide components. Binding to FKBP52 can be assayed using recombinant FKBP52 (Peattie et al., *Proc. Natl. Acad. Sci. USA* 89:10974–10978, 1992) instead of hsp90 and immobilized FK506 or FK506 analogs or hsp90. Binding to p23 can be assayed using recombinant human p23 (Johnson et al., *Mol. Cell. Biol.* 14:1956–1963, 1994) and immobilized hsp90. Purified hsp70 and recombinant p60 (Dittmar et al., *J. Biol. Chem.* 271:12833–12839, 1996) are also available for use in such binding assays.

Immunoassays can also be performed using conventional immunoassay methodologies and antibodies that are specific for steroid receptor complex components, e.g., antibodies against FKBP52 (Tai et al., *Biochem.* 25:5269–5275, 1986), hsp90 (Sanchez et al., *J. Biol. Chem.* 260:12398–12401, 1985; Catelli et al., *EMBO J.* 4:3131–3135, 1985; Schuh et al., *J. Biol. Chem.* 260:14292–14296, 1985), hsp70 (a serum that also recognizes hsp90 (Erhart et al. *Oncogene* 3:595–603, 1988), p23 (Johnson et al., *Mol. Cell. Biol.* 14:1956–1963, 1994), etc.

A well-accepted qualitative assay for receptor transformation, which involves dissociation of hsp90 from the receptor complex, is conversion of a receptor complex to a state that binds polyanions such as phosphocellulose (Kalimi et al., *J. Biol. Chem.* 250:1080–1086, 1975; Atger and Milgrom, *Biochem.* 15:4298–4304, 1976), ATP-Sepharose (Toft et al., *J. Steroid Biochem.* 7:1053–1059, 1976; Miller and Toft, *Biochem.* 17:173–177, 1978), and carboxymethol-Sephadex (Milgrom et al., *Biochem.* 12:5198–5205, 1973; Parchman and Litwack, *Arch. Biochem. Biophys.* 183:374–382, 1977).

An in vitro assay for nerve cell growth (neurite outgrowth) is provided in Example 1 below. In vivo assays for nerve regeneration are discussed in, for example, Gold et al., *Restor. Neurol. Neurosci.* 6:287–296, 1994; Gold et al., *J. Neurosci.* 15:7505–7516, 1995; Wang et al., *J. Pharmacol. Exp. Therapeutics* 282:1084–1093, 1997;. Gold et al., *Exp. Neurol.* 147:269–278, 1997; Gold et al., *Soc. Neurosci. Abst.* 23:1131, 1997, which examine the effects of systematic administration of a test compound on nerve regeneration and functional recovery following a crush injury to the rat sciatic nerve. Briefly stated, the right sciatic nerve of anaesthetized rats is exposed, and the nerve crushed twice using forceps at the level of the hip. Following the sciatic nerve crush, the test compound is administered to the rats, e.g., by subcutaneous injection or oral administration. Functional recovery is assessed by determining the number of days following nerve crush until the animal demonstrates onset of an ability to right its foot and move its toes, and the number of days until the animal demonstrates an ability to walk on its hind feet and toes. Nerve regeneration is also assessed by sampling tissues from the sciatic nerve at known (0.5 cm) distances from the crush site and examining the number of myelinated fibers and the size of axons by light microscopy. The axons are also examined by electron microscopy. Axonal areas of both myelinated and unmyelinated fibers are determined by tracing the axolemma using a digitizing tablet connected to a computer with appropriate software. Cumulative histograms are constructed from these data and mean values and standard errors are calculated to assess the effect of administration of the test compound on axonal areas.

"Geldanamycin derivatives". "Geldanamycin derivatives" include well-known synthetic derivatives (Schnur et al., *J. Med. Chem.* 38:3813–3820, 1995; Schnur et al., *J. Med. Chem.* 38:3806–3812, 1995). Geldanamycin derivatives preferably have the carbamate group and ansa ring of geldanamycin, which are necessary for activity (Schur et al., *J. Med. Chem.* 38:3806–3812, 1995), including modifications at the C23 methoxy and C22 methyl groups (Stebbins et al., *Cell* 89:239–250, 1997). Geldanamycin derivatives are also discussed in U.S. Pat. Nos. 5,3877,584, 4,261,989, and 3,987,035, and in Japanese Patent Applications 88041885, 56100766, and 89002593, for example.

"FK506 analogs". As used herein, the term "FK506 analogs" refers to compounds that are functionally analogous to FK506 in their ability to stimulate neuritic outgrowth. Such FK506 analogs, such as V-10, 367, retain the FKBP12 binding domain but lack the structural components of the effector domain (FIG. 1) and may either bind FKBP12 or be non-binding. V-10, 367, for example, binds FKBP12 with high affinity (<1 nM) (Armistead et al., *Acta Cryscallogr.* 51:522–528, 1995).

There has been an intense effort to design compounds that are structurally related to FK506 and that share the ability of FK506 to inhibit FKBP12 and thereby cause immunosuppression. See, for example: Bierer et al., *Science* 250:556–559, 1990; Van Duyne et al., *Science* 252:839–842, 1991; Van Duyne et al., *J. Mol. Biol.* 229:105–124, 1993; Hauske et al., *J. Med. Chem.* 35:4284–4296, 1992; Holt et al., *J. Am. Chem. Soc.* 115:9925–9938, 1993; Holt et al., *Bioorg. Med. Chem. Lett.* 3:1977–1980, 1993; Teague and Stocks, *Bioorg. Med. Chem. Lett.* 3:1947–1950, 1993; Wang et al., *Bioorg. Med. Chem. Lett.* 4:1161–1166, 1994; Yamashita et al., *Bioorg. Med. Chem. Lett.* 4:325–328, 1994; Stocks et al., *Bioorg. Med. Chem. Lett.* 4:1457–1460, 1994; Goulet et al., *Perspect. Drug Disc. Design* 2:145–162, 1994; Wilson et al., *Acta Cryst.* D51:511–521, 1995; Armistead et al., *Acta Cryst.* D51:522–528, 1995; U.S. Pat. Nos. 5,192, 773, 5,330,993, 5,516,797, 5,612,350, 5,614,547, 5,622,970, 5,654,332; and published international patent applications WO 92/00278, WO 92/04370, WO 92/19593, WO 92/21313, WO 94/07858, and WO 96/40633.

FK506 analogs include, but are not limited to:

(1) Compounds represented by the formula I (see U.S. Pat. Nos. 5,622,970, 5,516,797, 5,330,993, 5,192,773, and WO 92/00278 regarding synthesis of these compounds, the disclosures of which are incorporated herein by reference):

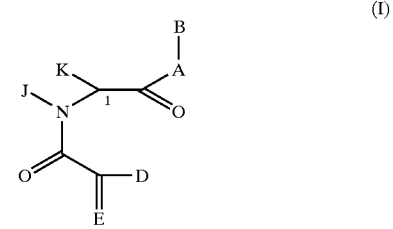

(I)

wherein A is O, NH, or N—(C1–C4 alkyl)

wherein B is hydrogen, CHL-Ar, (C1–C6)-straight or branched alkyl, (C2–C6)-straight or branched alkenyl, (C5–C7)-cycloalkyl, (C5–C7)-cycloalkenyl or Ar substituted (C1–C6)-alkyl or (C2–C6)-alkenyl, or

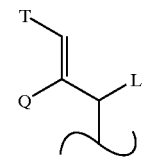

wherein L and Q are independently hydrogen, (C1–C6)-straight or branched alkyl or (C2–C6)-straight or branched alkenyl;

wherein T is Ar or substituted cyclohexyl with substituents at positions 3 and 4 that are independently selected from the group consisting of hydrogen, hydroxyl, O—(C1–C4)-alkyl or O—(C2–C4)-alkenyl and carbonyl;

wherein Ar is selected from the group consisting of 1-naphthyl, 2-naphthyl, 2-furyl, 3-furyl, 2-thienyl, 2-pyridyl, 3-pyridyl, 4-pyridyl and phenyl having one to three substituents that are independently selected from the group consisting of hydrogen, halo, hydroxyl, nitro, CF$_3$, (C1–C6)-straight or branched alkyl or (C2–C6)-straight or branched alkenyl, O—(C1–C4)-straight or branched alkyl or O—(C2–C4)-straight or branched alkenyl, O-benzyl, O-phenyl, amino and phenyl;

wherein D is U; E is either oxygen or CH-U, provided that if D is hydrogen, then E is CH-U or if E is oxygen, then D is not hydrogen;

wherein each U is independently selected from hydrogen, O—(C1–C4)-straight or branched alkyl or O—(C2–C4)-straight or branched alkenyl, (C1–C6)-straight or branched alkyl or (C2–C6)-straight or branched alkenyl, (C5–C7)-cycloalkyl or (C5–C7)-cycloalkenyl substituted with (C1–C4)-straight or branched alkyl or (C2–C4)-straight or branched alkenyl, 2-indolyl, 3-indolyl, [(C1–C4)-alkyl or (C2–C4)-alkenyl]-Ar or Ar;

wherein J is hydrogen or C1 or C2 alkyl or benzyl; K is (C1–C4)-straight or branched alkyl, benzyl or cyclohexylmethyl; or wherein J and K may be taken together to form a 5–7 membered heterocyclic ring that may contain an oxygen (O), sulfur (S), SO or SO$_2$ substituent therein; and the stereochemistry at position 1 is R or S.

(2) Compounds represented by the formula II (see U.S. Pat. No. 5,654,332, WO 94/07858, and WO 92/19593 for synthesis of these compounds, the disclosures of which are incorporated herein by reference):

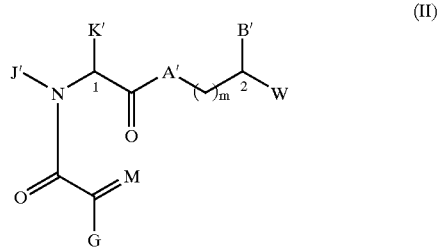

(II)

wherein A' is CH$_2$, oxygen, NH, or N—(C1–C4 alkyl);

wherein B' and W are independently hydrogen, Ar', (C1–C10)-straight or branched alkyl, (C2–C10)-straight or branched alkenyl or alkynyl, (C5–C7)-cycloalkyl substituted (C1–C6)-straight or branched alkyl, (C2–C6)-straight or branched alkenyl or alkynyl, (C5–C7)-cycloalkenyl substituted (C1–C6)-straight or branched alkyl, (C2–C6)-straight or branched alkenyl or alkynyl, or Ar' substituted (C1–C6)-straight or branched alkyl, (C2–C6)-straight or branched alkenyl or alkynyl wherein in each case, any one of the CH$_2$ groups of the alkyl, alkenyl, or alkynyl chains may be optionally replaced by a heteroatom selected from the group consisting of O, S, SO, SO$_2$, N, and NR, wherein R is selected from the group consisting of hydrogen, (C1–C4)-straight or branched alkyl, (C2–C4)-straight or branched alkenyl or alkynyl, and (C1–C4) bridging alkyl wherein a bridge is formed between the nitrogen and a carbon atom of the heteroatom-containing chain to form a ring, and wherein the ring is optionally fused to an Ar' group, or

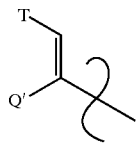

wherein Q' is hydrogen, (C1–C6)-straight or branched alkyl or (C2–C6)-straight or branched alkenyl or alkynyl;

wherein T' is Ar or substituted 5–7 membered cycloalkyl with substituents at positions 3 and 4 that are independently selected from the group consisting of oxo, hydrogen, hydroxyl, O—(C1–C4)-alkyl, and O—(C2–C4)-alkenyl;

wherein Ar' is a carboxcyclic aromatic group selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

wherein Ar' may contain one to three substituents that are independently selected from the group consisting of hydrogen, halogen, hydroxyl, hydroxymethyl, nitro, trifluoromethyl, trifluoromethoxy, (C1–C6)-straight or branched alkyl, (C2–C6)-straight or branched alkenyl, O—[(C1–C4)-straight or branched alkyl], O—[(C2–C4)-straight or branched alkenyl], O-benzyl, O-phenyl, 1,2-methylenedioxy, amino, carboxyl, N-[(C1–C5)-straight or branched alkyl or (C2–C5)-straight or branched alkenyl) carboxamides, N,N-di((C1–C5)-straight or branched alkyl or (C2–C5)-straight or branched alkenyl]carboxamides, N-morpholinocarboxamide, N-benzylcarboxamide, N-thiomorpholinocarboxamide, N-picolinoylcarboxamide, O—X, CH$_2$—(CH$_2$)$_q$—X, O—(CH$_2$)$_q$—X, (CH$_2$)$_q$—O—X, and CH=CH—X;

wherein X is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl; and q is 0–2;

wherein G is U';

wherein M is either oxygen or CH-U'; provided that if G is hydrogen, then M is CH-U' or if M is oxygen, then G is U';

wherein U' is hydrogen, O—[(C1–C4)-straight or branched alkyl] or O—[(C2–C4)-straight or branched alkenyl], (C1–C6)-straight or branched alkyl or (C2–C6)-straight or branched alkenyl, (C5–C7)-cycloalkyl or (C5–C7)-cycloalkenyl substituted with (C1–C4)-straight or branched alkyl or (C2–C4)-straight or branched alkenyl, [(C1–C4)-alkyl or (C2–C4)-alkenyl]-Y or Y;

wherein Y is selected from the group consisting of phenyl, 1-naphthyl, 2-naphthyl, indenyl, azulenyl, fluorenyl, anthracenyl, 2-pyrrolinyl, 3-pyrrolinyl, pyrolidinyl, 1,3-dioxolyl, 2-imidazolinyl, imidazolidinyl, 2H-pyranyl, 4H-pyranyl, piperidyl, 1,4-dioxanyl, morpholinyl, 1,4-dithianyl, thiomorpholinyl, piperazinyl, quinuclidinyl, and heterocyclic aromatic groups as defined for Ar' above;

wherein Y may contain one to three substituents that are independently selected from the group consisting of hydrogen, halogen, hydroxyl, hydroxymethyl, nitro, trifluoromethyl, trifluoromethoxy, (C1–C6)-straight or branched alkyl, (C2–C6)-straight or branched alkenyl, O—[(C1–C4)-straight or branched alkyl], O—[(C2–C4)-straight or branched alkenyl], O-benzyl, O-phenyl, 1,2-methylenedioxy, amino, and carboxyl;

wherein J' is hydrogen, (C1–C2) alkyl or benzyl; wherein K is (C1–C4)-straight or branched alkyl, benzyl or cyclohexylmethyl, or wherein J' and K may be taken together to form a 5–7 membered heterocyclic ring that may contain a heteroatom selected from the group consisting of O, S, SO and SO$_2$;

wherein m is 0–3; and wherein the stereochemistry at position 1 is R or S and the stereochemistry at position 2 is R or S.

(3) Compounds represented by the formula III (see Armistead et al., *Acta Cryst.* D51:522–528, 1995, including a discussion of selection of R and of the synthesis of these compounds, the disclosure of which is incorporated herein by reference):

(III)

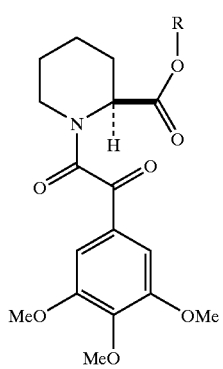

(4) Compounds represented by the formula IV (see WO 92/21313, including a discussion of the synthesis of these compounds, the disclosure of which is incorporated herein by reference):

(IV)

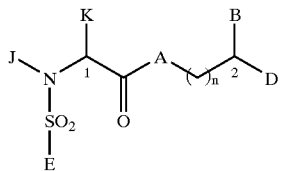

wherein A is $CH_2$, oxygen, NH or N—(C1–C4 alkyl);

wherein B and D are independently Ar, hydrogen, (C1–C6)-straight or branched alkyl, (C1–C6)-straight or branched alkenyl, (C1–C6)-straight or branched alkyl or alkenyl that is substituted with a (C5–C7)-cycloalkyl, (C1–C6)-straight or branched alkyl or alkenyl that is substituted with a (C5–C7)-cycloalkenyl, or Ar substituted (C1–C6)-straight or branched alkyl or alkenyl, wherein, in each case, one or two of the $CH_2$ groups of the alkyl or alkenyl chains may contain 1–2 heteroatoms selected from the group consisting of oxygen, sulfur, SO and $SO_2$ in chemically reasonable substitution patterns, or

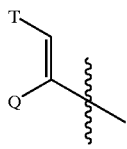

provided that both B and D are not hydrogen;

wherein Q is hydrogen, (C1–C6)-straight or branched alkyl or (C1–C6)-straight or branched alkenyl;

wherein T is Ar or substituted 5–7 membered cycloalkyl with substituents at positions 3 and 4 that are independently selected from the group consisting of hydrogen, hydroxyl, O—(C1–C4)-alkyl, O—(C1–C4)-alkenyl and carbonyl;

wherein Ar is selected from the group consisting of phenyl, 1-naphthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 that may contain in either or both rings a total of 1–4 heteroatoms independently selected from O, N and S;

wherein Ar may contain one to three substituents that are independently selected from the group consisting of hydrogen, halo, hydroxyl, nitro, trifluoromethyl, trifluoromethoxy, (C1–C6)-straight or branched alkyl, (C2–C6)-straight or branched alkenyl, O—(C1–C4)-straight or branched alkyl, O—(C2–C4)-straight or branched alkenyl, O-benzyl, O-phenyl, 1,2-methylenedioxy, amino, carboxyl and phenyl;

wherein E is (C1–C6)-straight or branched alkyl, (C1–C6)-straight or branched alkenyl, (C5–C7)-cycloalkyl, (C5–C7)-cycloalkenyl substituted with (C1–C4)-straight or branched alkyl or (C1–C4)-straight or branched alkenyl, [(C2–C4)alkyl or (C2–C4)-alkenyl)]-Ar or Ar (Ar as described above);

wherein J is hydrogen or C1 or C2 alkyl or benzyl; K is (C1–C4)-straight or branched alkyl, benzyl or cyclohexylmethyl; or wherein J and K may be taken together to form a 5–7 membered heterocyclic ring that may contain an oxygen, sulfur, SO or $SO_2$ substituent therein; and;

wherein n is 0–3; and wherein the stereochemistry at position 1 is R or S and the stereochemistry at position 2 being R or S.

(5) Compounds represented by the formula V (see WO 92/04370, including a discussion of the synthesis of these compounds, the disclosure of which is incorporated herein by reference)

(V)

wherein A is NH, O, S, or CH;

wherein if A is NH, O, or S, B is PCO— or POCO—, where P is a C1–C6 straight or branched alkyl or alkenyl group, a C5–C6 cycloalkyl or cycloalkenyl, or a methyl substituted with a C5–C6 cycloalkyl, C5–C6 cycloalkenyl, phenyl, 1-naphthyl, 2-naphthyl, 9-fluorenyl, or 1-adamantyl;

wherein if A is CH, then B is connected via a trans double bond and is a C2–C4 straight or branched alkyl or alkenyl group, or is a methyl or ethyl substituted with either a C5–C6 cyclic alkyl group or Ar, where Ar is selected from the group consisting of 1-naphthyl, 2-naphthyl, 2-furyl, 3-furyl, 2-thienyl, phenyl and phenyl having one to three substituents that are independently selected from the group consisting of: hydroxyl, halo, nitro, $CF_3$, C1–C4 straight or branched alkyl or alkenyl, O—(C1–C4) straight or branched alkyl or alkenyl, and Ar, where Ar is selected from the group consisting of 1-naphthyl, 2-naphthyl, 2-furyl, 3-furyl, 2-thienyl, phenyl and phenyl having one to three substituents that are independently selected from the group consisting of: hydroxyl, halo, nitro, $CF_3$, C1–C4 straight or branched alkyl or alkenyl, O—(C1–C4) straight or branched alkyl or alkenyl; wherein no more than two Ar groups may be linked together;

wherein D is hydrogen, C1–C4 straight or branched alkyl or alkenyl, hydroxy, tert-butyloxy, benzyloxy, 4-benzyloxyphenyl, cyclohexyl, —$(CH_2)_n$—$CO_2$-Q, where n=0 or 1 and Q is methyl, ethyl, i-propyl, t-butyl, benzyl, 1-naphthyl, 2-naphthyl, or cyclohexyl; or Ar, where Ar is selected from the group consisting of 1-naphthyl, 2-naphthyl, 2-furyl, 3-furyl, 2-thienyl, phenyl and phenyl having one to three substituents that are independently selected from the group consisting of: hydroxyl, halo, nitro, $CF_3$, C1–C4 straight or branched alkyl or alkenyl, O—(C1–C4) straight or branched alkyl or alkenyl, and Ar, where Ar is selected from the group consisting of 1-naphthyl, 2-naphthyl, 2-furyl, 3-furyl, 2-thienyl, phenyl and phenyl having one to three substituents that are independently selected from the group consisting of: hydroxyl, halo, nitro, $CF_3$, C1–C4 straight or branched alkyl or alkenyl, O—(C1–C4) straight or branched alkyl or alkenyl; wherein no more than two Ar groups may be linked together;

wherein E and K are independently hydrogen or methyl;

wherein G is either methyl or ethyl; J is hydrogen, C1–C6 straight or branched alkyl or alkenyl, C6-C6 cycloalkyl or cycloalkenyl, sulfhydryl, hydroxy, phenyl, 3-indolyl, or benzyl; wherein G and J may be connected by a bond to form a cycle of 5 or 6 members;

wherein L is O or an α-amino acid residue attached via the α-nitrogen, and selected from the group consisting of: alanine, 2-aminobutyric acid, valine, norvaline, leucine, norleucine, isoleucine, phenylalanine, cyclohexylalanine, tryptophan, 1-naphthylalanine, 2-naphthylalanine, threonine (side chain benzyl or tert-butyl ether), methionine, or serine (side chain benzyl or tert-butyl ether);

wherein if L is O, then M is C1–C6 straight or branched alkyl or alkenyl, or —$(CH_2)_n$—Ar, where n=1–6 and Ar is selected from the group consisting of: 1-naphthyl, 2-naphthyl, 2-furyl, 3-furyl, 2-thienyl, phenyl and phenyl having one to three substituents that are independently selected from the group consisting of: hydroxyl, halo, nitro, $CF_3$, C1–C4 straight or branched alkyl or alkenyl, O—(C1–C4) straight or branched alkyl or alkenyl, and Ar, wherein Ar is selected from the group consisting of: 1-naphthyl, 2-naphthyl, 2-furyl, 3-furyl, 2-thienyl, phenyl and phenyl having one to three substituents that are independently selected from the group consisting of: hydroxyl, halo, nitro, $CF_3$, C1–C4 straight or branched alkyl or alkenyl, O—(C1–C4) straight or branched alkyl or alkenyl; wherein no more than two Ar groups may be linked together;

wherein if L is an amino acid, then M is O—(C1–C4) straight or branched alkyl, O-benzyl, NH-Phenyl, or NH-4-nitrophenyl and is attached to the amino acid carbonyl;

the stereochemistry at all positions being R or S, and preferably the stereochemistry is S at L if L is an α-amino acid, and at those positions marked with asterisks; however, when J is sulfhydryl, the preferred stereochemistry of the asterisked position immediately adjacent to the nitrogen is R.

(6) Compounds represented by the formula VI (see WO 96/40633, including a discussion of the synthesis of these compounds, the disclosure of which is incorporated herein by reference):

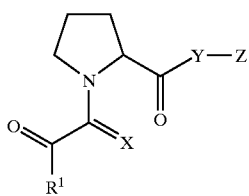

(VI)

wherein, R1 is selected from the group consisting of a C1–C9 straight or branched chain alkyl or alkenyl group optionally substituted with C3–C8 cycloalkyl, C3 or C5 cycloalkyl, C5–C7 cycloalkenyl, or Arl, where said alkyl, alkenyl, cycloalkyl or cycloalkenyl groups may be optionally substituted with C1–C4 alkyl, C1–C4 alkenyl, or hydroxy, where Ar1 is selected from the group consisting of 1-naphthyl, 2-naphthyl, 2-indolyl, 3-indolyl, 2-furyl, 3-furyl, 2-thiazolyl, 2-thienyl, 3-thienyl, 2-, 3-, 4-pyridyl and phenyl, having one to three substituents that are independently selected from the group consisting of hydrogen, halo, hydroxyl, nitro, trifluoromethyl, C1–C6 straight or branched alkyl or alkenyl, C1–C4 alkoxy or C1–C4 alkenyloxy, phenoxy, benzyloxy, and amino;

wherein X is selected from the group consisting of oxygen, sulfur, methylene ($CH_2$), or $H_2$;

wherein Y is selected from the group consisting of oxygen or $NR_2$, where $R_2$ is hydrogen or C1–C6 alkyl; and wherein Z is selected from the group consisting of C2–C6 straight or branched chain alkyl or alkenyl, wherein the alkyl chain is substituted in one or more positions with $Ar_1$ as defined above, C3–C8 cycloalkyl, cycloalkyl connected by a C1–C6 straight or unbranched alkyl or alkenyl chain and $Ar_2$, where $Ar_2$ is selected from the group consisting of 2-indolyl, 3-indolyl, 2-furyl, 3-furyl, 2-thiazolyl, 2-thienyl, 3-thienyl, 2-, 3-, or 4-pyridyl, and phenyl, having one to three substituents that are independently selected from the group consisting of hydrogen, halo, hydroxyl, nitro, trifluoromethyl, C1–C6 straight or branched alkyl or alkenyl, C1–C4 alkoxy or C1–C4 alkenyloxy, phenoxy, benzyloxy, and amino;

wherein Z may also be the fragment:

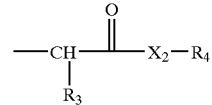

where $R_3$ is selected from the group consisting of straight or branched alkyl C1–C8 optionally substituted with C3–C8 cycloalkyl, or $Ar_1$ as defined above, and unsubstituted $Ar_1$;

$X_2$ is O or $NR_5$, where $R_5$ is selected from the group consisting of hydrogen, C1–C6 straight or branched alkyl and alkenyl;

$R_4$ is selected from the group consisting of phenyl, benzyl, C1–C5 straight or branched alkyl or alkenyl, and C1–C5 straight or branched alkyl or alkenyl substituted with phenyl;

wherein the stereochemistry at position 1 is R or S.

Also encompassed are pharmaceutically acceptable derivatives of the FK506 analogs, including, but not limited to, any pharmaceutically acceptable salt, ester, salt of an ester, or any other derivative which, upon administration to a patient, is capable of providing directly or indirectly a non-binding FK506 analog or a metabolite or residue thereof that has the desired neurotrophic activity. Included within the scope of the invention are enantiomers, the racemic form, and diastereoisomeric mixtures. Enantiomers and diastereoisomers can be separated by conventional methods.

Formulae I–VI above represent compounds that have a wide range of binding affinities for FKBP12. The mechanism for neurotrophic activity of FK506 presented herein indicates that the effectiveness of FK506 and FK506 analogs in stimulating nerve cell growth is unrelated to their ability to bind FKBP12. Instead, their effectiveness in stimulating nerve cell growth relates to ability of such compounds to bind FKBPS2 and subsequently interfere with the interaction of FKBPS2 and hsp90 in a steroid receptor complex, e.g., by competing for FKBP52 binding to hsp90, altering the conformation of FKBP52, etc.

A "non-binding FK506 analog" is defined as an FK506 analog that does not bind to FKBP12. Preferably, such FK506 analogs bind FKBP12 with an apparent $K_d$ of greater than 10 μM as measured using well-known assays, and preferably greater than 30 μM, and more preferably greater than 100 μM. Values for the apparent $K_d$ can be determined, for example, by a competitive LH-20 binding assay performed as described, for example, in Harding et al., *Nature* 341:758–760, 1989 (using 32-[1-$^{14}$C]-benzoyl FK506 as a reporting ligand; Siekierka et al., *Nature* 341:755–757, 1989, using [$^3$H]dihydro-FK506 as a reporting ligand); and U.S. Pat. No. 5,654,332.

Alternatively, a "non-binding FK506 analog" is defined as an FK506 analog that does not significantly inhibit FKBP12 rotamase activity when administered to a patient at dosage levels of about 0.01 to about 100 mg/kg body weight/day. Assays for inhibition of FKBP12 rotamase activity are described in Harding et al. (*Nature* 341:758–760, 1989), Siekierka et al., *Nature* 341:755–757, 1989, and U.S. Pat. No. 5,654,332, for example. The assays of Harding et al. and Siekierka et al. employ a reaction mixture that includes the cis form of N-succinyl-Ala-Ala-Pro-Phe-p-nitroanilide, FKBP12, a test compound, and chymotrypsin, and spectrophotometrically measure the release of p-nitroanilide as a result of isomerization of the substrate.

Non-binding FK506 analogs are non-immunosuppressive, as can be demonstrated by well-known assays, e.g., as discussed in U.S. Pat. No. 5,516,797, WO 92/21313, WO 92/19593, and WO 92/04370.

Non-binding FK506 analogs can be used in the form of salts preferably derived from inorganic or organic acids and bases, including, but not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include, but are not limited to, ammonium salts, alkali metal salts (such as sodium and potassium salts), alkaline earth metal salts (such as calcium and magnesium salts), salts with organic bases (such as dicyclohexylamine salts), N-methyl-D-glucamine, and salts with amino acids (such as arginine, lysine, etc.). Basic nitrogen-containing groups can be quaternized, e.g., with such agents as lower alkyl halides (such as methyl, ethyl, propyl; and butyl chlorides, bromides, and iodides), dialkyl sulfates (such as dimethyl, diethyl, dibutyl, an diamyl sulfates), long-chain halides (such as decyl, lauryl, myristyl, and stearyl chlorides, bromides, and iodides), aralkyl halides (such as benzyl and phenethyl bromides), etc. Water or oil-soluble or dispersible products are produced thereby.

Non-binding FK506 analogs can be modified by appending appropriate functionalities by well-known methods to enhance selected biological properties, including increasing penetration of the analogs into a given cellular compartment (e.g., blood, lymphatic system, central nervous system, etc.), increase oral availability, increase solubility to permit administration by injection, alter metabolism, and alter rate of excretion, for example.

Preferably, the non-binding FK506 analogs have a molecular weight below about 750 atomic mass units (a.m.u.) (as the parent compound, although the salts of such compounds can have higher molecular weights).

"Effective amount" or "nerve growth stimulating amount." An "effective amount" or a "nerve growth stimulating amount" of a composition according to the invention is an amount sufficient to achieve a statistically significant promotion of nerve cell growth or regeneration compared to a control. Nerve cell growth or nerve regeneration can be readily assessed using an in vitro assay, e.g., the assay described in the Examples below. Alternatively, nerve cell growth or regeneration can be determined in an in vivo assay or by direct or indirect signs of nerve cell growth and regeneration in a patient. Preferably, the increase in nerve cell growth or regeneration is at least 10%, preferably at least 30%, and most preferably 50% or more compared to a control. Preferred dosage levels are between about 0.1 to about 400 mg/kg per day of the FK506 analog for subcutaneous delivery. For oral administration, preferred dosage levels are between about 0.01 to about 40 mg/kg/day.

Therapeutic and Prophylactic Uses

Pharmaceutical compositions according to the invention can be periodically administered to a mammalian patient (e.g., a human patient), in need of such treatment, to promote neuronal regeneration and functional recovery and to stimulate neurite outgrowth and thereby to treat various neuropathological states, including damage to peripheral nerves and the central nervous system caused by physical injury (e.g., spinal cord injury and trauma, sciatic or facial nerve lesion or injury), disease (e.g., diabetic neuropathy), cancer chemotherapy (e.g., by vinca alkaloids and doxorubicin), brain damage associated with stroke and ischemia associated with stroke, and neurological disorders including, but not limited to, various peripheral neuropathic and neurological disorders related to neurodegeneration including, but not limited to: trigeminal neuralgia, glossopharyngeal neuralgia, Bell's palsy, myasthenia gravis, muscular dystrophy, amyotrophic lateral sclerosis, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies such as those caused by lead, acrylamides, gamma-diketones (glue-sniffer's neuropathy), carbon disulfide, dapsone, ticks, porphyria, Gullain-Barré syndrome, Alzheimer's disease, Parkinson's disease, and Huntington's chorea.

In addition, pharmaceutical compositions according to the present invention display a wide range of other therapeutic or prophylactic properties, including, treatment of stroke (see, e.g., Sharkey and Butcher, *Nature* 371:336–339, 1994, Vagita et al., *Life Sciences* 59:1643–1650, 1996; Tokime et al., *Neurosci. Lett.* 206:81–84, 1996; Drake et al., *Acta. Physiol. Scand.* 158:155–159, 1996; and Kuroda et al., *Neurosci. Res. Comm.* 19:83–90, 1996), AIDS dementia (see, e.g., Dawson and Dawson, *Adv. Neuroimmunol.* 4:167–173, 1994; and Sekigawa et al., *J. Clin. Immunol.* 15:312–317, 1995); hair growth (Yamamoto et al., *J. Investig. Dermatol.* 102:160–164, 1994; Jiang et al., *J. Investig. Dermatol.* 104:523–525, 1995); and connective tissue disorders (see e.g., Steinmann et al., *J. Biol. Chem.* 266:1299–1303, 1991), and as a male contraceptive (see e.g., Hisatomi et al., *Toxicology* 109:75–83, 1996).

A transection of a periphal nerve or a spinal cord injury can be treated by administering a nerve growth stimulating amount of a non-FKBP12-binding nerve growth promoting agent to the mammal and grafting to the peripheral nerve or spinal cord an allograft (Osawa et al., *J. Neurocytol.* 19:833–849, 1990; Buttemeyer et al., *Ann. Plastic Surgery* 35:396–401, 1995) or an artificial nerve graft (Madison and Archibald, *Exp. Neurol.* 128:266–275, 1994; Wells et al., *Exp. Neurol.* 146:395–402, 1997). The space between the transected ends of the peripheral nerve or spinal cord is preferably filled with a non-cellular gap-filling material such as collagen, methyl cellulose, etc., or cell suspensions that promote nerve cell growth, such as Schwann cells (Xu et al., J. Neurocytol. 26:1–16, 1997), olfactory cells, and sheathing cells (Li et al. Science 277:2000–2002, 1997). The nerve growth promoting agent can be included together with with such cellular or non-cellular gap-filling materials.

Pharmaceutical Formulations

Pharmaceutical formulations according to the present invention encompass formulations comprising (1) an amount (for example, a unit dosage) of an NGPA together with (2) one or more well-known non-toxic pharmaceutically acceptable excipients, including carriers, diluents, and/or adjuvants, and optionally (3) one or more biologically active ingredients. Standard pharmaceutical formulation techniques are used, such as those disclosed in *Remington's Pharmaceutical Sciences,* Mack Publishing Co., Easton, Pa. (latest edition).

A pharmaceutical formulation according to the invention includes one or more NGPAs and can also include, for example, one or more other biologically active ingredients, including, but not limited to FK506 or an FKBP12-binding FK506 analogs or one or more other neurotrophic agents, including, for example, NGF, IGF-1, aFGF, bFGF, PDGF, BDNF, CNTF, GDNF, NT-3, and NT 4/5; and so on.

It is preferred that the pharmaceutical formulation includes an amount of a neurotrophic agent(s), preferably NGF, such that the patient receives a dosage of between about 0.01 to 100 μg/kg body weight/day of the neurotrophic agent, or that the neurotrophic agent be administered separately, e.g., in separate single or multiple dosage forms, preferably concurrently, consecutively, or within less than about five hours of each other.

The compositions can be in the form of tablets, capsules, powders, granules, lozenges, liquid or gel preparations, such as oral, topical, or sterile parenteral solutions or suspensions (e.g., eye or ear drops, throat or nasal sprays, etc.), transdermal patches, and other forms known in the art.

Such pharmaceutical compositions can be administered systemically or locally in any manner appropriate to the treatment of a given condition, including orally, parenterally, rectally, nasally, buccally, vaginally, topically, optically, by inhalation spray, or via an implanted reservoir. The term "parenterally" as used herein includes, but is not limited to subcutaneous, intravenous, intramuscular, intrasternal, intrasynovial, intrathecal, intrahepatic, intralesional, and intracranial administration, for example, by injection or infusion. For treatment of the central nervous system, the pharmaceutical compositions preferably readily penetrate the blood-brain barrier when peripherally administered or are administered intraventricularly.

Pharmaceutically acceptable carriers include, but are not limited to, ion exchangers, alumina, aluminum stearate, lecithin, serum proteins (such as human serum albumin), buffers (such as phosphates), glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat, for example.

Tablets and capsules for oral administration can be in a form suitable for unit dose presentation and can contain conventional pharmaceutically acceptable excipients. Examples of these include binding agents such as syrup, acacia, gelatin, sorbitol, tragacanth, and polyvinylpyrrolidone; fillers such as lactose, sugar, corn starch, calcium phosphate, sorbitol, or glycine; tableting lubricants, such as magnesium stearate, talc, polyethylene glycol, or silica; disintegrants, such as potato starch; and dispersing or wetting agents, such as sodium lauryl sulfate. The tablets can be coated according to methods well known in normal pharmaceutical practice. Oral liquid preparations can be in the form of, for example, aqueous or oily suspensions, solutions, emulsions, syrups or elixirs, or can be presented as a dry product for reconstitution with water or other suitable vehicle before use. Such liquid preparations can contain conventional additives such as suspending agents, e.g., sorbitol, syrup, methyl cellulose, glucose syrup, gelatin, hydrogenated edible fats, emulsifying agents, e.g., lecithin, sorbitan monooleate, or acacia; non-aqueous vehicles (including edible oils), e.g., almond oil, fractionated coconut oil, oily esters such as glycerine, propylene glycol, or ethyl alcohol; preservatives such as methyl or propyl p-hydroxybenzoate or sorbic acid, and, if desired, conventional flavoring or coloring agents.

Pharmaceutical compositions according to the present invention can also be administered parenterally in a sterile aqueous or oleaginous medium. The composition can be dissolved or suspended in a non-toxic parenterally-acceptable diluent or solvent, e.g., as a solution in 1,3-butanediol. Adjuvants such as local anesthetics, preservatives, and buffering agents can also be dissolved in the vehicle. Commonly used vehicles and solvents include water, physiological saline, Hank's solution, Ringer's solution, and sterile, fixed oils, including synthetic mono- or di-glycerides, etc. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as Ph. Helv or a similar alcohol.

For topical application, the drug may be made up into a solution, suspension, cream, lotion, ointment in a suitable aqueous or non-aqueous vehicle. Additives may also be included, e.g., buffers such as sodium metabisulphite or disodium edeate; preservatives such as bactericidal and fungicidal agents, including phenyl mercuric acetate or nitrate, benzalkonium chloride or chlorhexidine, and thickening agents, such as hypromellose.

The dosage unit involved depends, for example, on the condition treated, nature of the formulation, nature of the condition, embodiment of the claimed pharmaceutical compositions, mode of administration, and condition and weight of the patient. Dosage levels on the order of about 0.1 to about 400 mg/kg per day of the active ingredient are useful in the treatment of the conditions listed above.

The invention will be better understood by reference to the following examples, which are intended to merely illustrate the best mode now known for practicing the invention. The scope of the invention is not to be considered limited thereto, however.

EXAMPLES

FK506 and Geldanamycin Promote Nerve Regeneration by a Common Mechanism

Materials and Methods

Cell cultures. SH-SY5Y human neuroblastoma cells were maintained in DMEM medium (GIBCO) supplemented with 10% fetal calf serum (SIGMA), 50 IU/mL penicillin, and 50 mg/mL streptomycin (GIBCO) at 37° C. in 7% $CO^2$. Cells were plated in six-well plates at $1\times10^6$ cells/well and treated with 0.4 mM aphidicolin (SIGMA). At five days, cells were washed, treated with nerve growth factor (NGF) (Boehringer Mannheim, Indianapolis, Ind.) at 10 ng/mL (to induce process outgrowth) in the presence or absence of FK506 (1 and 10 nM) (Calbiochem-Novabiochem Int'l., La Jolla, Calif.) and/or geldanamycin (0.1, 1, and 10 nM) (Calbiochem-Novabiochem, La Jolla, Calif.). Media was changed at 96 hours and replaced with fresh media with the compounds (NGF plus FK506 and/or geldanamycin) for an additional 72 hours (total time, 168 hours). The top 50% of axonal lengths were selected for statistical analysis. All experiments were run in duplicate wells and repeated at least twice for reproducibility.

Light morphometry of neurite lengths. For analysis of process length, cells 20 fields per well) were randomly photographed at 72 and 168 hours. Neurite lengths were measured on photographic prints using a Houston Instrument HI-PAD digitizing tablet connected to an IBM XT computer with appropriate software (Bioquant IV, R&M Biometrics, Nashville, Tenn.); only those processes greater than two times the cell body length were measured. Data from identically treated wells were not different and were therefore combined. Mean values and histograms were constructed from these data. Histograms were compared using a Mann-Whitney U test, which makes no assumptions about the shape of the distribution.

Preparation of FK506 and geldanamycin. FK506 (mol. wt. 822) and geldanamycin (mol. wt. 561) were dissolved in DMEM medium.

Results

In a first set of experiments, SH-SY5Y neuroblastoma cells were plated in 6-well plates with DMEM plus 15% FCS and differentiated with NGF (10 ng/ml). The effects of various concentrations of geldanamycin and FK506 on neurite growth, alone and in combination, were tested. The mean lengths of neuritic processes of untreated and treated cells are shown in Table 1.

Figure 2:
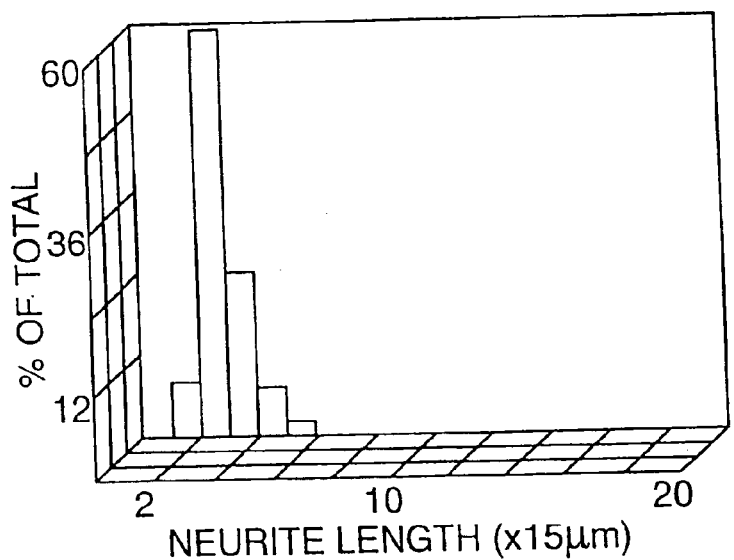
FIGS. 2–8 are histograms showing the stimulation of growth of SH-SY5Y cells by geldanamycin and FK506 in the presence of NGF (10 ng/mL) 168 hours after treatment.
Figure 3:
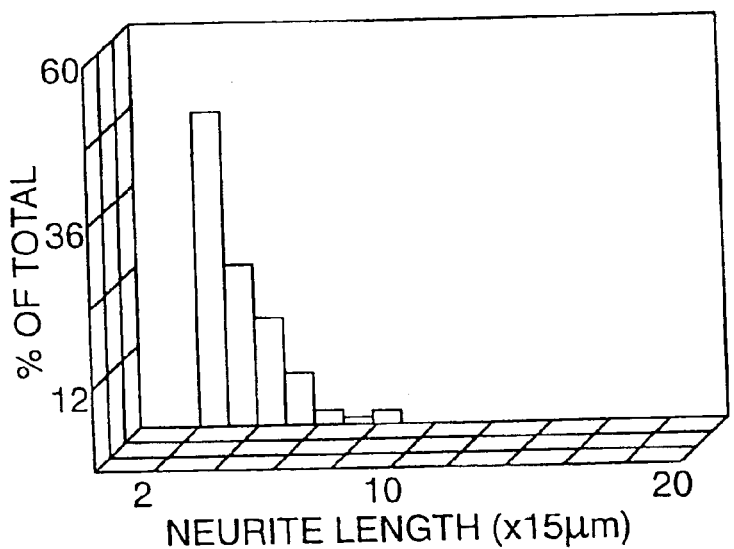
Figure 4:
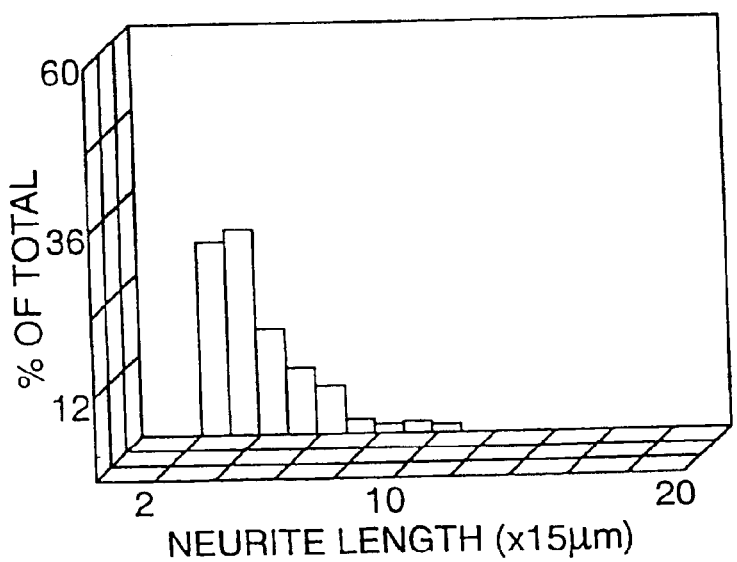
Figure 5:
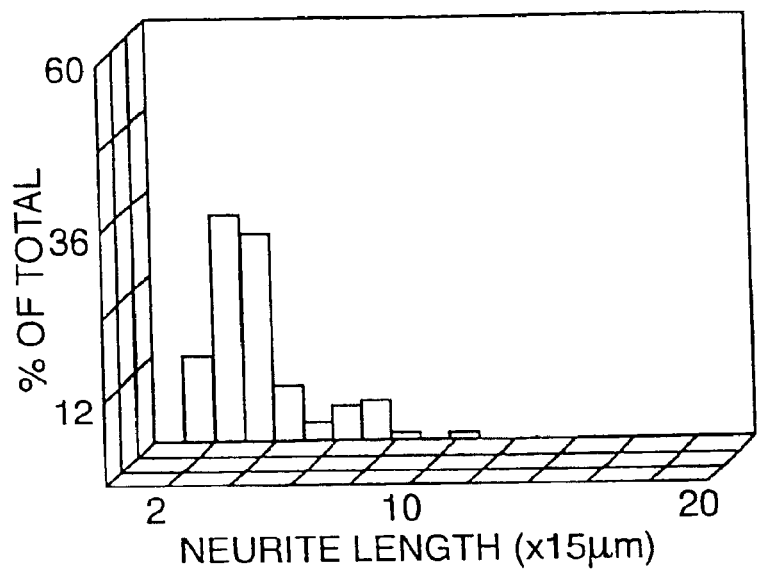
Figure 6:
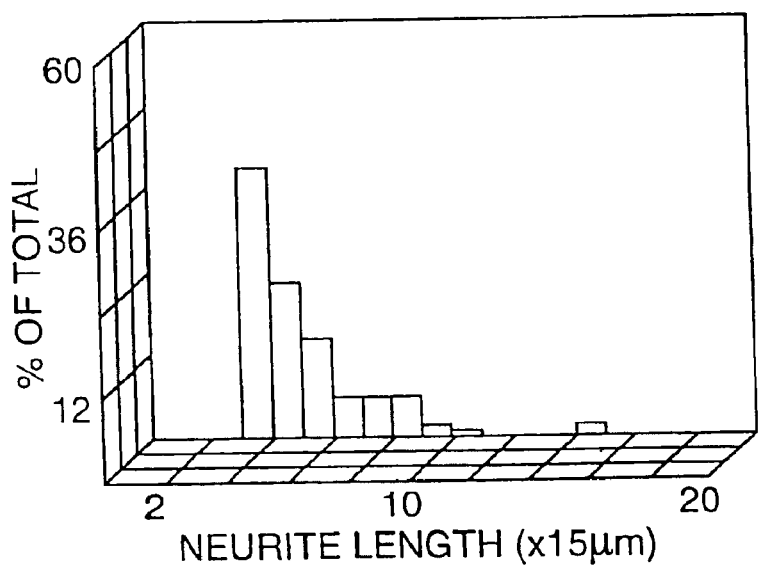
Figure 7:
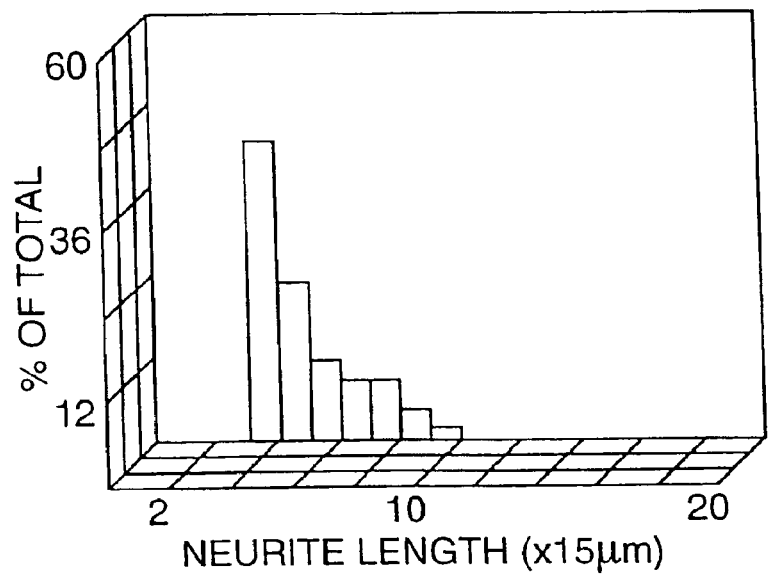

The cells developed long axonal-like processes upon exposure to NGF (10 ng/mL) as measured at 168 hours after treatment. NGF more than doubled the mean length of the processes compared to untreated cells (compare FIGS. 1 and 2). An even greater increase in the length of the processes was observed when the cells were exposed to geldanamycin at 1 nM in the presence of NGF (FIG. 3). However, geldanamycin at 10 nM had no effect (FIG. 4). FK506 (10 nM) stimulated neurite outgrowth in the presence of NGF (FIG. 5) to a greater degree than geldanamycin at either 1 nM or 10 nM. In combination with FK506 (10 nM), geldanamycin (FIG. 6, 1 nM; FIG. 7, 10 nM) inhibited the effect of FK506 in a concentration-dependent fashion.

Figure 8:
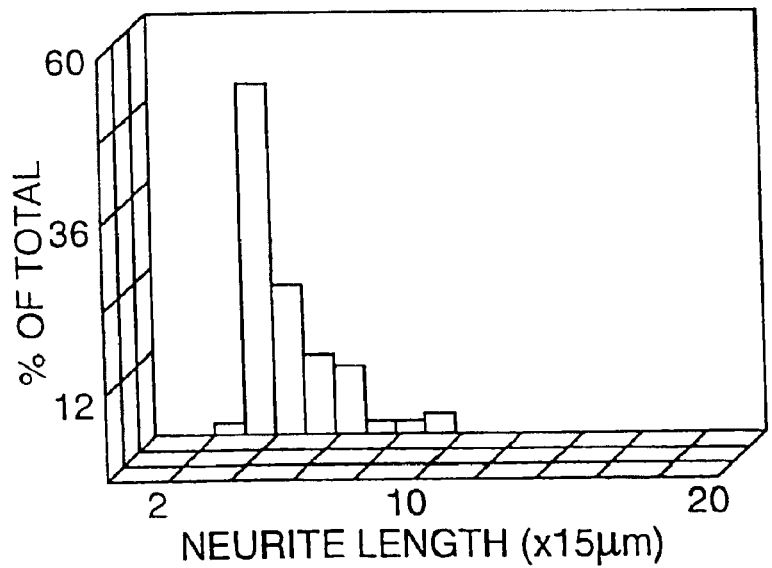
Figure 9:
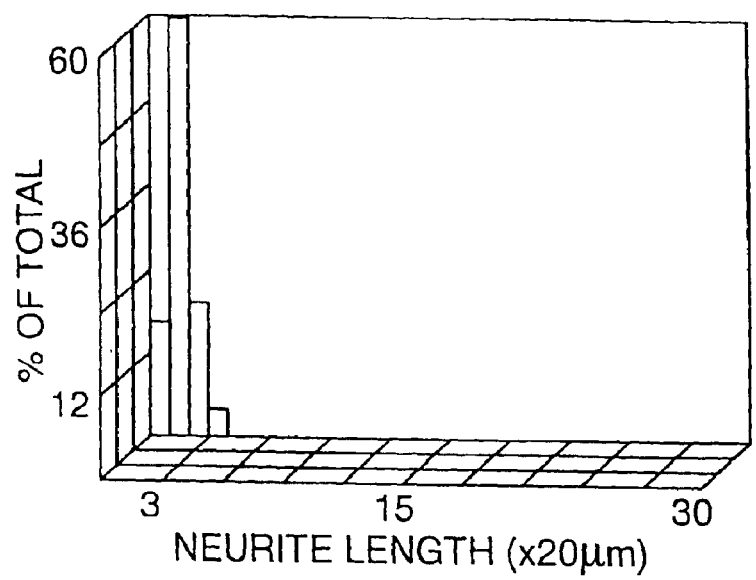
FIGS. 9–15 are histograms showing the stimulation of growth of SH-SY5Y cells by geldanamycin and FK506 in the presence of NGF (10 ng/mL) 168 hours after treatment.
Figure 10:
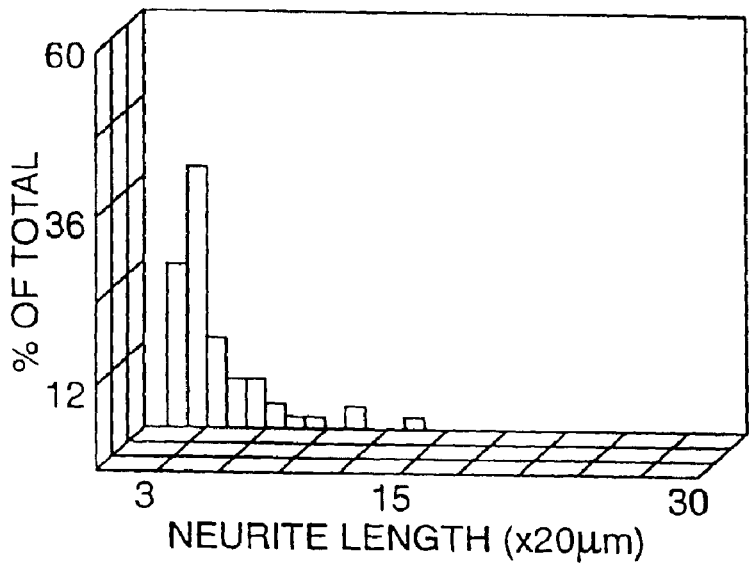
Figure 11:
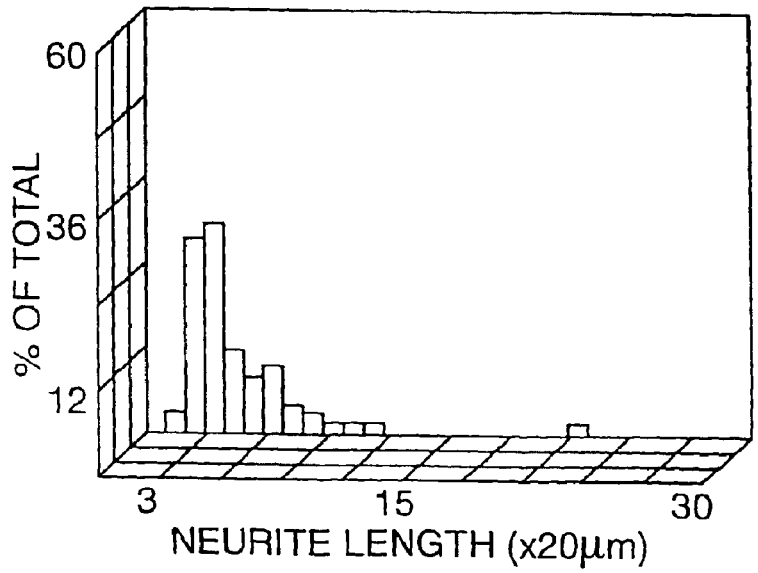
Figures 12, 13:
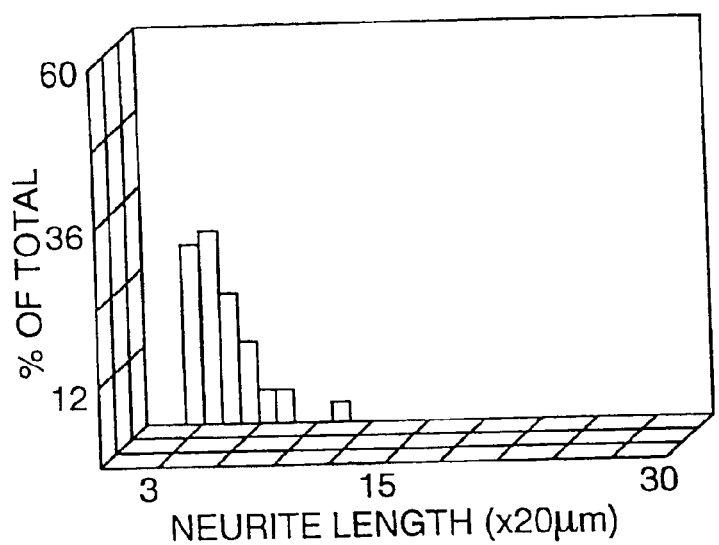
Figure 14:
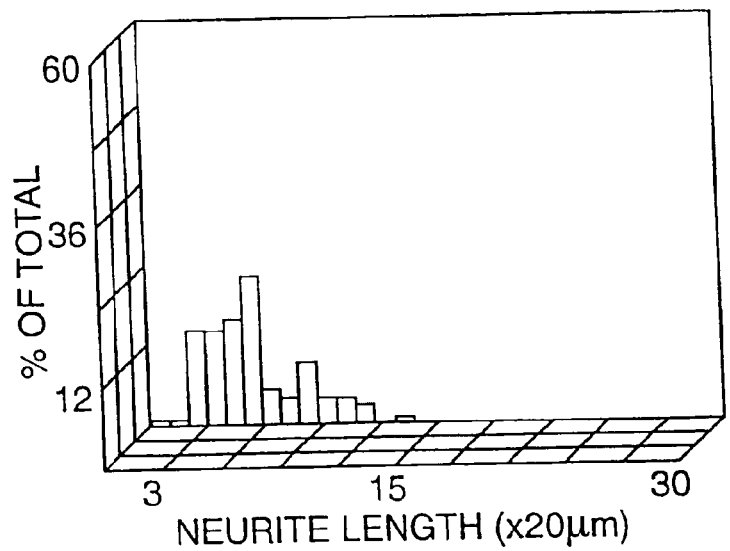
Figure 15:
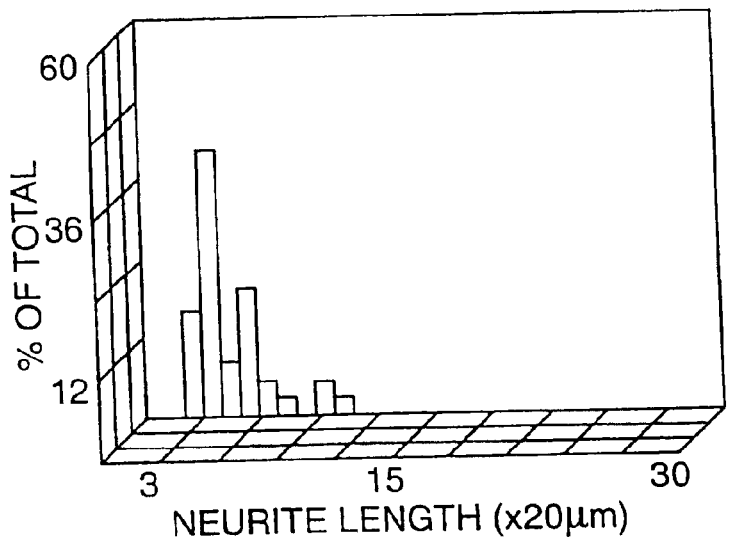

In a second set of experiments, lower concentrations of geldanamycin and FK506 were tested, alone and in combination. The mean lengths of neuritic processes of untreated and treated cells are shown in Table 2. NGF-treated cells (FIG. 9) had mean neuritic lengths more than double the mean length of untreated control cells (FIG. 8). Nerve growth stimulation was observed with FK506 (1 nM, FIG. 10; 10 nM, FIG. 11) in the presence of NGF and geldanamycin (0.1 nM, FIG. 12) in the presence of NGF. The lower concentration of FK506 (1 nM) was more effective in stimulating neurite outgrowth than the higher concentration (10 nM), and geldanamycin at 0.1 nM was even more effective in stimulating neurite outgrowth than FK506 at either 1 nM or 10 nM. Combined treatment with geldanamycin (0.1 nM) and FK506 (1 nM, FIG. 13; 10 nM, FIG. 14) in the presence of NGF showed that the effects of geldanamycin and FK506 were additive, particularly at the lower FK506 concentration (FIG. 13).

Geldanamycyin and FK506 each stimulate neurite outgrowth in a concentration-dependent fashion. Taken together, the similar effects of geldanamycin and FK506 in stimulating neurite outgrowth, their additive effects at low concentrations, and their inhibitory effects at high concentrations (like high concentrations of either compound alone), demonstrate that the two compounds act on nerve cells via a common mechanism. That mechanism likely involves an interaction of both compounds with components of steroid receptor complexes. FKBP12 does not appear to play a role in the stimulation of neurite outgrowth by either geldanamycin or FK506.

In further experiments, we have found that estrogen (10 nM) and dexamethasone (10 nM) increased neurite outgrowth (without NGF) of SH-SY5Y cells and produced an additive effect on neurite outgrowth (neurotrophic action) with FK506 (10 nM).

This invention has been detailed both by example and by direct description. It should be apparent that one having ordinary skill in the relevant art would be able to surmise equivalents to the invention as described in the claims which follow but which would be within the spirit of the foregoing description. Those equivalents are to be included within the scope of this invention.

TABLE 1

Mean Length of Top 50% of Neuritic Processes of SH-SY5Y 168 Hours After Treatment with Geldanamycin (1 nM or 10 nM) and/or FK506 (10 nM) in the Presence of NGF

| Treatment | Mean Length ($\mu$M) | S.E.M. |
| --- | --- | --- |
| Untreated | 41.61 | 1.25 |
| NGF (10 ng/mL) | 53.99 | 2.26 |
| Geldanamycin (1 nM) + NGF (10 ng/mL) | 64.00 | 2.36 |
| Geldanamycin (10 nM) + NGF (10 ng/mL) | 54.81 | 2.10 |
| FK506 (10 nM) + NGF (10 ng/mL) | 77.82 | 2.70 |
| Geldanamycin (1 nM) + FK506 (10 nM) + NGF (10 ng/mL) | 72.63 | 2.01 |
| Geldanamycin (10 nM) + FK506 (10 nM) + NGF (10 ng/mL) | 67.41 | 1.67 |

TABLE 2

Mean Length of Top 50% of Neuritic Processes of SH-SY5Y 168 Hours After Treatment with Geldanamycin (0.1 nM) and/or FK506 (1 nM or 10 nM) in the Presence of NGF

| Treatment | Mean Length ($\mu$M) | S.E.M. |
| --- | --- | --- |
| Untreated | 31.86 | 1.56 |
| NGF (10 ng/mL) | 70.38 | 6.61 |
| Geldanamycin (0.1 nM) + NGF (10 ng/mL) | 98.07 | 5.72 |
| FK506 (1 nM) + NGF (10 ng/mL) | 89.92 | 6.40 |
| FK506 (10 nM) + NGF (10 ng/mL) | 82.68 | 5.22 |
| Geldanamycin (0.1 nM) + FK506 (1 nM) + NGF (10 ng/mL) | 110.51 | 6.13 |
| Geldanamycin (0.1 nM) + FK506 (10 nM) + NGF (10 ng/mL) | 92.50 | 6.40 |

What is claimed is:

1. A method of improving nerve growth into a partial transection of a spinal cord, comprising:
  introducing into the transection NGF and a non-cellular gap filling agent that includes a therapeutically effective amount of a benzoquinone ansamycin that binds to a polypeptide component of a steroid receptor complex other than a steroid binding portion of the complex, wherein the NGF and benzoquinone ansamycin are present in a therapeutically sufficient amount to interfere with association or promote dissociation of hsp90 from the complex, and promote nerve growth into the spinal cord.

2. A method of promoting nerve growth a mammal having a partially transected spinal cord, the method comprising:
  administering to the mammal a pharmaceutical composition comprising a nerve growth stimulating amount of a non-FKBP12-binding agent that binds to a polypeptide component of a steroid receptor complex other than a steroid hormone binding portion of the complex wherein the agent interferes with association or promotes dissociation of hsp90 with the complex and promotes nerve growth, thereby promoting nerve growth.

3. The method of claim 2 wherein the non-FKBP12-binding agent is administered in a gap-filling composition comprising the non-FKBP12-binding agent.

4. The method of claim 2, wherein the agent is selected from the group consisting of a non-FKBP12-binding FK506 analog, a benzoquinone ansamycin, a peptide comprising a sequence of a selected polypeptide component of the steroid receptor complex at a site of interaction between the selected component and another polypeptide component of the steroid receptor complex, an antibody that binds to a polypeptide component of the complex, and combinations thereof.

5. The method of claim 4, wherein the agent is a benzoquinone ansamycin.

6. The method of claim 5, wherein the benzoquinone ansamycin is a geldanamycin derivative.

7. The method of claim 2, wherein the agent binds to FKBP12 with an apparent $K_d$ of greater than 10 $\mu$M.

8. The method of claim 7, wherein the agent binds FKBP12 with an apparent $K_d$ of greater than 30 $\mu$M.

9. The method of claim 8, wherein the agent binds FKBP12 with an apparent $K_d$ of greater than 100 $\mu$M.

10. The method of claim 2, wherein the agent is selected from the group consisting of a peptide comprising a sequence from a component of the steroid receptor complex which peptide inhibits assembly or promotes dissociation of the steroid receptor complex, an antibody that binds to a component of the steroid receptor complex and prevents assembly or promotes dissociation of the steroid receptor complex, a benzoquinone ansamycin, or an FK506 analog which binds to FKBP12 with a $K_d$ of at least 10 $\mu$M, and combinations thereof.

11. The method of claim 2, further comprising grafting to the spinal cord an allograft or artificial nerve graft.

12. The method of claim 2, wherein the agent is in combination with a neurotrophic factor, other than the agent.

13. The method of claim 12, wherein the neurotrophic factor is NGF, estrogen, or dexamethasone.

14. The method of claim 2, further comprising administering a second neurotrophic agent in an amount that promotes nerve growth in combination with the pharmaceutical composition.

15. A method of promoting nerve repair in a mammal having a spinal cord injury, the method comprising:
  administering to the mammal a pharmaceutical composition comprising a nerve repair stimulating amount of an agent, other than FK506, that binds to a polypeptide component of a steroid receptor complex other than a steroid hormone binding portion of the complex, and which promotes hsp90 dissociation or inhibits hsp90 association with the complex, and promotes repair of the injury, wherein the spinal cord injury is a partial transection.

16. The method of claim 15, further comprising grafting to the partial transection an allograft, and the agent is administered in a therapeutically sufficient amount that promotes growth of the nerve graft.

17. The method of claim 16, further comprising grafting an artificial nerve graft to the partial transection.

18. The method of claim 17, wherein the artificial nerve graft is a collagen nerve graft, and the agent is administered in a therapeutically sufficient amount that promotes growth of the partially transected spinal cord.

19. The method of claim 15, further comprising applying a therapeutically effective amount of the agent directly to an injured area of the spinal cord to promote nerve growth at the injured area.

20. The method of claim 19, wherein applying the agent directly to the injured area comprises contacting the partial transection with a therapeutically effective amount of the agent to promote nerve growth at the partial transection.

21. The method of claim 15, further comprising filling the partial transection with a gap filling material that includes a therapeutically sufficient amount of the agent to promote nerve growth into the spinal cord.

22. The method of claim 21, wherein the gap filling material comprises a cellular or non-cellular gap filling material.

23. The method of claim 22, wherein the gap filling material is a non-cellular gap filling material.

24. The method of claim 23, wherein the non-cellular gap filling material is collagen.

25. The method of claim 15, wherein the nerve repair stimulating agent is administered along a path for new nerve growth.

26. The method of claim 15, wherein the agent is:
(a) an FK506 analog
(b) a benzoquinone ansamycin
(c) a peptide comprising a sequence of a polypeptide component of the steroid receptor complex at a site of interaction between the selected component and another polypeptide component of the steroid receptor complex; or
(d) an antibody that binds to a polypeptide component of the steroid receptor complex.

27. The method of claim 26 wherein the agent is non-immunosuppressive.

28. The method of claim 26, wherein the agent is an FK506 analog.

29. The method of claim 26, wherein the agent is a benzoquinone ansamycin.

30. The method of claim 14, wherein the second neurotrophic agent is NGF, IGF-1, aFGF, bFGF, PDGF, BDNF, CNTF, GDNF, NT-3, or NT 4/5.

* * * * *

UNITED STATES PATENT AND TRADEMARK OFFICE
CERTIFICATE OF CORRECTION

PATENT NO. : 6,881,409 B2  
APPLICATION NO. : 10/656701  
DATED : April 19, 2005  
INVENTOR(S) : Bruce G. Gold It is certified that error appears in the above-identified patent and that said Letters Patent is hereby corrected as shown below:

In column 4, line 46, the word "FKS20" should be --FK520--.  
In column 4, line 49, the word "FKBPS2" should be --FKBP52--.  
In column 10, line 11, the word "N,N-di((" should be --N,N-di[--.  
In column 14, line 57, the word "FKBPS2" should be --FKBP52--.  
In column 14, line 58, the word "FKBPS2" should be --FKBP52--.

In Claim 2, column 21, line 38, change "a" to --in a--.

Signed and Sealed this

Twenty-second Day of July, 2008

JON W. DUDAS  
*Director of the United States Patent and Trademark Office*

SEQUENCE LISTING

```
<160> NUMBER OF SEQ ID NOS: 2

<210> SEQ ID NO 1
<211> LENGTH: 8
<212> TYPE: PRT
<213> ORGANISM: Sylvilagus sp.

<400> SEQUENCE: 1

Glu Asp Leu Thr Asp Asp Glu Asp
1               5

<210> SEQ ID NO 2
<211> LENGTH: 8
<212> TYPE: PRT
<213> ORGANISM: Rattus sp.

<400> SEQUENCE: 2

Arg Lys Thr Lys Lys Lys Ile Lys
1               5
```